US008968758B2

(12) United States Patent
Yeung et al.

(10) Patent No.: US 8,968,758 B2
(45) Date of Patent: Mar. 3, 2015

(54) MATERIAL FOR FORMING A MULTI-LEVEL ANTIMICROBIAL SURFACE COATING AND ITS PREPARATION

(71) Applicant: The Hong Kong University of Science and Technology Technology Transfer Center, Hong Kong (CN)

(72) Inventors: King Lun Yeung, Hong Kong (CN); Wai Kin Leung, Hong Kong (CN)

(73) Assignee: The Hong Kong University of Science and Technology, Hong Kong (CN)

( * ) Notice: Subject to any disclaimer, the term of this patent is extended or adjusted under 35 U.S.C. 154(b) by 0 days.

(21) Appl. No.: 14/253,547

(22) Filed: Apr. 15, 2014

(65) Prior Publication Data

US 2014/0341961 A1 Nov. 20, 2014

Related U.S. Application Data

(62) Division of application No. 12/631,732, filed on Dec. 4, 2009, now Pat. No. 8,741,325.

(60) Provisional application No. 61/193,712, filed on Dec. 18, 2008.

(51) Int. Cl.
*A01N 25/26* (2006.01)
*A01N 25/04* (2006.01)
*A01N 59/00* (2006.01)
*A01N 59/20* (2006.01)
*A01N 59/16* (2006.01)

(52) U.S. Cl.
CPC ............... *A01N 25/26* (2013.01); *A01N 59/00* (2013.01); *A01N 25/04* (2013.01); *A01N 59/16* (2013.01); *A01N 59/20* (2013.01)
USPC ........ 424/405; 424/78.17; 424/663; 424/618; 424/630; 424/638

(58) Field of Classification Search
USPC ....................................................... 424/78.02
See application file for complete search history.

(56) References Cited

U.S. PATENT DOCUMENTS

2008/0199420 A1* 8/2008 Wendel et al. ............. 424/78.02

* cited by examiner

*Primary Examiner* — Walter Webb
(74) *Attorney, Agent, or Firm* — WPAT, P.C.; Anthony King

(57) ABSTRACT

The present invention provides a method for preparing a material in the form of liquid for forming an antimicrobial surface coating with multi-level antimicrobial properties, comprising: encapsulating one or more volatile or gaseous biocides in two or more amphiphilic block copolymers to obtain a w/o/w double emulsion, and mixing the w/o/w double emulsion with one or more nonvolatile biocides, each of which is selected from the group consisting of a metal containing biocide, triclosan, a carboxylic acid, a sugar acid and a combination thereof.

12 Claims, 16 Drawing Sheets

_US 8,968,758 B2_

MATERIAL FOR FORMING A MULTI-LEVEL ANTIMICROBIAL SURFACE COATING AND ITS PREPARATION

CROSS-REFERENCE TO RELATED APPLICATION

This application is a divisional of U.S. patent application Ser. No. 12/631,732, filed Dec. 4, 2009, which claims the benefit of the priority pursuant to 35 U.S.C. §119(e) of U.S. Provisional Patent Application No. 61/193,712, filed Dec. 18, 2008. The contents of the prior applications are incorporated herein by their entireties.

BACKGROUND OF THE INVENTION

Microorganisms are ubiquitous in our environment. Although many are harmless and even beneficial, some are well-known pathogens, while others can elicit allergenic responses in human. The World Health Organization (WHO) reported that one of the most common routes for transmission of infectious diseases is by indirect contact with surfaces contaminated with infectious droplets produced by the patients' coughing, sneezing or talking. Many microbes, including viruses can survive for days on surfaces. For instance, influenza virus can remain viable for 24-48 hours, while parainfluenza and SARS viruses are known to survive for hours and days on most surfaces. Some pathogens are known to transmit through fomites. When fomites touch contaminated surfaces by pathogens, the pathogens transmit through the fomites. Therefore, regular cleaning and disinfection are important for breaking the chain of infection, and the use of antimicrobial surface coating provides additional safeguard against the disease transmission.

Many metals including silver, copper and brass possess intrinsic germicidal properties that can kill many pathogenic microorganisms upon contact [Fang, H. P., *Pure & Appl. Chem.* 1997, 69, 2425-2429]. Nanosilvers, photocatalytic $TiO_2$ and surface tethered bactericides (e.g., quarternary ammonium compounds (QACs), phosphonium salts) are known to be used as contact-killing antimicrobial surface coatings in recent years. However, the anti-microbial properties of these materials diminish rapidly when the surface is fouled by dirt and contaminants, thus requiring frequent cleaning to maintain their effectiveness.

It has also been developed to store antibiotics, biocides (e.g., phenols, halogens) and metals (e.g., silver ions) in bulk materials and coatings for a slow, gradual and continuous release into the environment providing a sustained "release-killing" until the content is exhausted. Cohen's group (Li, Z. et al., *Langmuir* 2006, 22, 9820-9823) employed layer-by-layer, self-assembly method to produce a two-level antibacterial coating with both "release-killing" and "contact-killing" capabilities based on stored silver salt and surface grafted quaternary ammonium, while Ho et al. (Ho, C. H. et al., *Adv. Mater* 2004, 16, 957-961) used a polymer film to immobilize nanosilver to achieve both "contact- and release-killing" effects, while a grafted layer of polyethylene glycol repelled the adhesion of bacteria. However, the adhesion of pathogens (such as microorganisms), dirt and/or contaminants on surfaces is still a problem in the antimicrobial coating with the both contact- and release-killing effects. Accordingly, a multi-level antimicrobial surface coating is still desired.

BRIEF SUMMARY OF THE INVENTION

The present invention provides a solution to the problem of the currently developed antimicrobial surface coatings.

One object of the invention is to provide a material for forming an antimicrobial surface coating with multi-level antimicrobial properties, which comprises one or more volatile or gaseous biocides, one or more nonvolatile biocides, and one or more polymers, wherein the volatile or gaseous biocides are encapsulated in the polymers to provide a sustained release of the volatile or gaseous biocides.

Another object of the invention is to provide a method for preparing the material for forming an antimicrobial surface coating with multi-level antimicrobial properties, which the method comprises: encapsulating one or more volatile or gaseous biocides in one or more polymers to provide a sustained release of the volatile or gaseous biocides, and mixing with one or more nonvolatile biocides.

One further object of the invention is to provide a method of disinfecting an article or a subject, comprising: providing a material for forming an antimicrobial surface coating with multi-level antimicrobial properties, which comprises one or more volatile or gaseous biocides, one or more nonvolatile biocides, and one or more polymers, wherein the volatile or gaseous biocides are encapsulated in the polymers to provide a sustained release of the volatile or gaseous biocides; and applying onto the article or subject with the material to form an antimicrobial surface coating with the release-killing, contact-killing and anti-adhesion effects.

BRIEF DESCRIPTION OF THE DRAWINGS

The foregoing summary, as well as the following detailed description of the invention, will be better understood when read in conjunction with the appended drawings. It should be understood, however, that the invention is not limited to the precise arrangements and instrumentalities shown.

In the drawings.

DETAILED DESCRIPTION OF THE INVENTION

Figure 1:
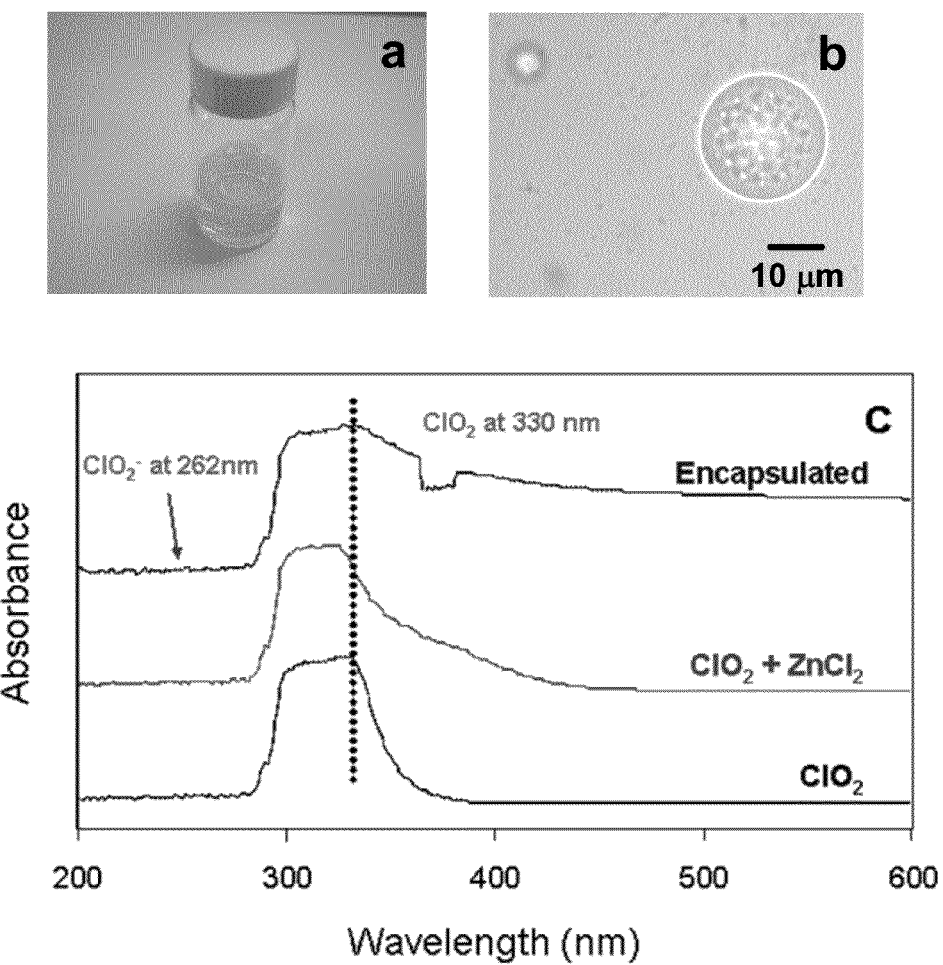
FIG. 1 is a photograph showing (a) polymer-encapsulated $ClO_2$ w/o/w emulsion after a month in storage and the (b) optical microscope picture and (c) UV-visible spectrum of the prepared antimicrobial w/o/w double emulsion formulation B ($ClO_2$+$ZnCl_2$) and formulation A without zinc (Encapsulated), with the pure, non-encapsulated chlorine dioxide solution ($ClO_2$) for reference standard.

The present invention provides a material for forming an antimicrobial surface coating with multi-level antimicrobial properties, which comprise one or more volatile or gaseous biocides, one or more nonvolatile biocides, and one or more polymers, wherein the volatile or gaseous biocides are encapsulated in the polymers to provide a sustained release of the volatile or gaseous biocides.

According to the invention, the volatile or gaseous biocides include but are not limited to dissolved chlorine dioxide (ClO$_2$), dissolved chlorine, chlorinated compounds, alcoholic and phenolic compounds, and their solid and/or liquid precursors, and combination thereof. In one example of the invention, the volatile biocide is dissolved chlorine dioxide and its precursors. In another example of the invention, the volatile biocide is a combination of chlorine dioxide, a chlorite salt and chlorine.

According to the invention, the nonvolatile biocides include but are limited to metal containing biocides, triclosan, carboxylic acids, sugar acids or the combination thereof. One example of carboxylic acids is citric acid and one example of sugar acids is ascorbic acid. In one embodiment of the invention, the nonvolatile biocides are metal containing biocides. According to the invention, each of the metal containing biocides is selected from the group consisting of one or more of Group VII, IB, IIB, IVA and IVB metal containing compounds and salts thereof, and the combination thereof. In some examples of the invention, the metal containing biocide is a trace metal-containing compound or salts thereof, such as silver, copper or zinc-containing compound.

According to the invention, the term "polymers" as used herein refers to "polymers", "polymeric surfactants" or the combination thereof, which form an emulsion encapsulating the biocides so that the biocides may be released slowly, gradually and continuously into the surrounding environment. In one example of the invention, the polymers and/or polymeric surfactants form a double-layer emulsion, such as a water-in-oil-in-water (w/o/w) double emulsion, in which the volatile or gaseous biocides are encapsulated to provide a sustained release of the biocides. According to the invention, each of the polymers is selected from the group consisting of an amphiphilic block copolymers and the combination thereof. In some examples of the invention, the amphiphilic block copolymer is an amphiphilic di- or tri-blocks copolymer such as poloxamers (e.g. commercial Pluronics, or Tetronics), or the combination thereof.

According to the invention, the coating as formed by the material exhibits multi-level antimicrobial properties including release-killing, contact-killing and anti-adhesion through (1) a sustained release of the volatile biocide(s) at a sufficient amount to disinfect and inhibit microbial growth, (2) an increased release of the biocide(s) on contact with infectious droplets, and (3) a nanostructure of the nonvolatile biocide(s) as formed on surfaces to inactivate and prevent the adhesion of microorganisms when applied.

In one particular example of the invention, the material or composition for forming an antimicrobial surface coating comprises an volatile oxidative biocide and a nonvolatile biocide, such as one of Group VII, IB, IIB, IVA and IVB metal containing compounds, and one or more polymers to form a water-in-oil-in-water (w/o/w) double emulsion in which the both biocides are encapsulated, whereby the polymers interact with the volatile oxidizing biocide and metal-containing compounds, and then the metal-containing nanostructures are formed and deposited on the external surface of the w/o/w double emulsion.

In the invention, the formation of the metal-containing nanostructures is believed to involve redox reaction involving the oxidative biocide and the metal-containing compounds such as metal salts, depending on their respective redox potential, either metallic or metal oxide nanostructures to be obtained. The polymers act as typical surfactants and control the growth of the nanostructures preventing the formation of large particles so that the nanostructures are formed in-situ and deposited on the surface of the emulsions.

In one embodiment of the invention, the water-in-oil-in-water (w/o/w) double emulsion comprises a first water phase, an oil phase, and a second water phase composed from the polymers in a ratio of 1:0.5~2:2~20 by volume proportion. In one example of the invention, the first water phase contains from about 10 ppm to about 70 vol. % of the volatile biocide(s), depending on the efficacy and duration of use and more than one volatile biocides used; the oil phase contains a low volatile oil compatible with the biocides that may react with the oil phase and denature it, and may also contain a second biocide such as nonvolatile carboxylic or sugar acid, and a fragrance for olfactory cue and aesthetic purposes; and the second water phase encapsulated by the outermost polymers contains one or more nonvolatile metal-containing biocides providing contact-killing properties, wherein the metals contained in the nonvolatile biocides are equivalent to or less than about 5000 ppm, preferably less than about 100 ppm. In one example, the nonvolatile biocide contained in the second water phase is triclosan at the amount of about 3% by weight of the total material. The first water phase, the oil phase and the second water phase are separated by the polymers or polymeric surfactants. According to the invention, the outermost polymers separating the oil-phase and the second water phase also displays anti-adhesion properties against microorganisms, wherein the minimum concentrations of the polymers or polymeric surfactants are determined by their critical micelle concentrations and characteristics of the surfactants.

In one embodiment of the invention, the material of the invention is applied onto an article to form on the article a surface coating providing multi-level effects including a "release-killing" effect by a sustained release of the volatile biocides from the w/o/w emulsion prepared from the polymers or polymeric surfactants at a room condition to disinfect and inhibit microbial growth, and a "contact-killing" effect by an increased release of the nonvolatile metal-containing biocides when the surface coating contacts with or is contaminated by infectious droplets, and an "anti-adhesion" effect by the metal-containing nanostructures as formed on surfaces by an interaction between the metal-containing biocides and the outermost polymers.

Furthermore, the invention provides a method for preparing the material for forming an antimicrobial surface coating with multi-level antimicrobial properties, which the method comprises encapsulating one or more volatile or gaseous biocides in one or more polymers to provide a sustained release of the volatile or gaseous biocides, and mixing with one or more nonvolatile biocides. In one example of the invention, the nonvolatile biocides may be encapsulated together with the volatile or gaseous biocides in the polymers.

In addition, the invention provides a method of disinfecting an article or a subject, comprising: providing a material for forming an antimicrobial surface coating with multi-level antimicrobial properties, which comprises one or more volatile or gaseous biocides, one or more nonvolatile biocides, and one or more polymers, wherein the volatile or gaseous biocides are encapsulated in the polymers to provide a sustained release of the volatile or gaseous biocides; and applying onto the article or subject with the material to form an antimicrobial surface coating with the release-killing, contact-killing and anti-adhesion effects.

The present invention is further illustrated by the following examples, which are provided for the purpose of demonstration rather than limitation.

Example 1

Preparation of the Antimicrobial w/o/w Double Emulsion Composition A

An aqueous solution of $ClO_2$ was activated by HCl (0.45 mol/L) in a molar ratio of 1:1. Twenty-five milliliters of the above solution were suspended in lemon oil (10% (v/v) essential oil from natural extract dissolved in paraffin solvent and had a low evaporation rate of 0.1 based on BuAc=1 (Note: $H_2O$=0.3)). 25 ml of 5% (w/v) Pluronic P123 ($EO_{20}PO_{70}EO_{20}$; MW 5750 g/mol; HLB (hydrophilic lipophilic balance) of 8; purchased from BASF, Germany) surfactant solution was added to above mixture with stiffing (i.e., 400 rpm). The resulting emulsion was then added to an aqueous suspension of 2.5 g Pluronic F127 ($EO_{106}PO_{70}EO_{106}$; MW 12600 g/mol; HLB of 22; purchased from BASF, Germany) dissolved in 50 ml deionized water at a stiffing rate of 200 rpm to give a 1:1:2 w/o/w double emulsions.

Example 2

Preparation of the Antimicrobial w/o/w Double Emulsion Composition B

An aqueous solution of $ClO_2$ was activated by HCl (0.45 mol/L) in a molar ratio of 1:1. Twenty-five milliliters of the above solution were suspended in lemon oil (10% (v/v) essential oil from natural extract dissolved in paraffin solvent and had a low evaporation rate of 0.1 based on BuAc=1 (Note: $H_2O$=0.3)). 25 ml of 5% (w/v) Pluronic P123 ($EO_{20}PO_{70}EO_{20}$; MW 5750 g/mol; HLB (hydrophilic lipophilic balance) of 8; purchased from BASF, Germany) surfactant solution was added to above mixture with stiffing (i.e., 400 rpm). The resulting emulsion was then added to an aqueous suspension of 2.5 g Pluronic F127 ($EO_{106}PO_{70}EO_{106}$; MW 12600 g/mol; HLB of 22; purchased from BASF, Germany) dissolved in 50 ml deionized water at a stirring rate of 200 rpm to give a 1:1:2 w/o/w double emulsions. A 0.25 ml of 50 mM $ZnCl_2$ (99%, Aldrich) was added and the final emulsion. In other preparation, $CuCl_2$ (99%, Aldrich), $AgNO_3$ (99%, Aldrich), or metal salts (i.e., combinations of $Zn^{2+}$, $Cu^{2+}$ and $Ag^+$) could be substituted for $ZnCl_2$.

Example 3

Preparation of the Antimicrobial w/o/w Double Emulsion Composition C

An aqueous solution of $ClO_2$ was activated by HCl (0.45 mol/L) in a molar ratio of 1:1. Twenty-five milliliters of the above solution were suspended in paraffin solvent and had a low evaporation rate of 0.1 based on BuAc=1 (Note: $H_2O$=0.3). 25 ml of 5% (w/v) Pluronic P123 ($EO_{20}PO_{70}EO_{20}$; MW 5750 g/mol; HLB (hydrophilic lipophilic balance) of 8; purchased from BASF, Germany) surfactant solution was added to above mixture with stiffing (i.e., 400 rpm). The resulting emulsion was then added to an aqueous suspension of 2.5 g Pluronic F127 ($EO_{106}PO_{70}EO_{106}$; MW 12600 g/mol; HLB of 22; purchased from BASF, Germany) dissolved in 50 ml deionized water at a stirring rate of 200 rpm to give a 1:1:2 w/o/w double emulsions. A 500 ppm $CuCl_2$ (99%, Aldrich) and 100 ppm Ascorbic Acid (99%, Aldrich) was added.

Example 4

Characterization of the Antimicrobial w/o/w Double Emulsion (1) The w/o/w double emulsion ranges from white opaque to transparent and is stable for prolonged storage (see FIG. 1a);

(2) The w/o/w double emulsion was examined under optical microscope to observe polymer-encapsulated $ClO_2$. FIG. 1b is an image of the polymer-encapsulated $ClO_2$ according to the invention. Tiny emulsion capsules measuring 10-20 microns in diameter were observed under the optical microscope, and it was possible to see faint traces of the smaller micron-sized w/o emulsion within the capsules;

(3) The stored amount of $ClO_2$ was determined by the iodometric titration using 0.1 M sodium thiosulfate ($Na_2S_2O_3$, RDH) and starch indicator;

(4) The stored $ClO_2$ was inspected by UV-Vis spectrophotometer (Ultrospec 4300 pro) for the presence of other oxychlorine species such as chlorite and hydrochlorite. The spectrum in FIG. 1c was taken between 200 to 600 nm at a resolution of 0.5 nm. The UV-visible spectroscopy of the double emulsion detected $ClO_2$ (330 nm).

Analysis of Composition A by Microscopy

Figure 2:
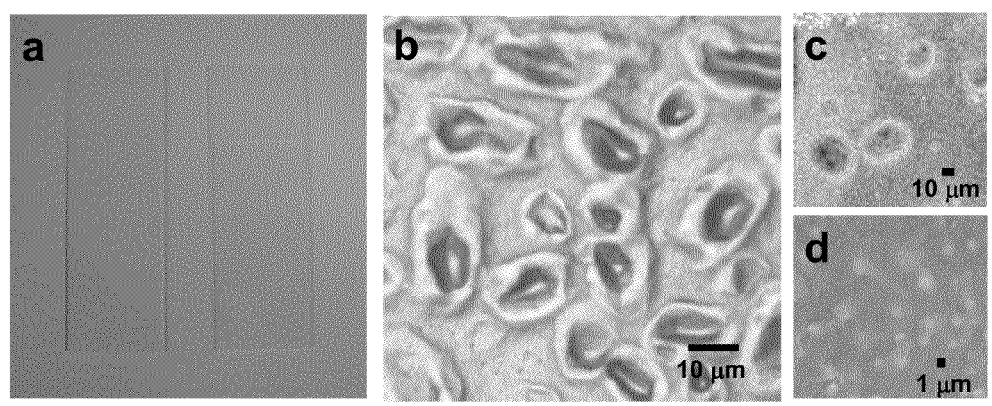
FIG. 2 is a photograph with (a) images of glass slide with (left) and without (right) a coating of the polymer-encapsulated $ClO_2$, (b) optical and (c) & (d) scanning electron microscope pictures of the coated glass showing a uniform surface coating (b) consisting of globules (c) containing 0.5 to 1 micron-sized emulsion clusters (d).

The coated w/o/w double emulsion deposited to form a transparent and tactilely smooth coating on surface as shown in FIG. 2a. Syneresis which is a common problem for gels and hydrogels was not observed.

The coated w/o/w double emulsion was examined by an optical microscope (Olympus BH2-MJLT) and a JEOL 6300 scanning electron microscope at an acceleration voltage of 10-15 kV. FIG. 2b shows optical micrographs of the surface at 100× magnification, and the coating displays uniform features that are reminiscent of the deposited microcapsules. A closer examination by scanning electron microscope at a higher magnification revealed the globular shapes of the deposited microcapsules (FIG. 2c) and the smaller 0.5-1 μm capsules they contained (FIG. 2d).

Anatomy of the Composition B with Zinc Chloride Salt

The antimicrobial w/o/w double emulsion composition B containing 30 ppm zinc chloride salt was deposited on a transmission electron microscope grid. The coating was observed under the JEOL JEM 2010 high resolution transmission electron microscope at an accelerating voltage of 200 kV, and beam current of 100 $pA.cm^{-2}$.

Figure 3:
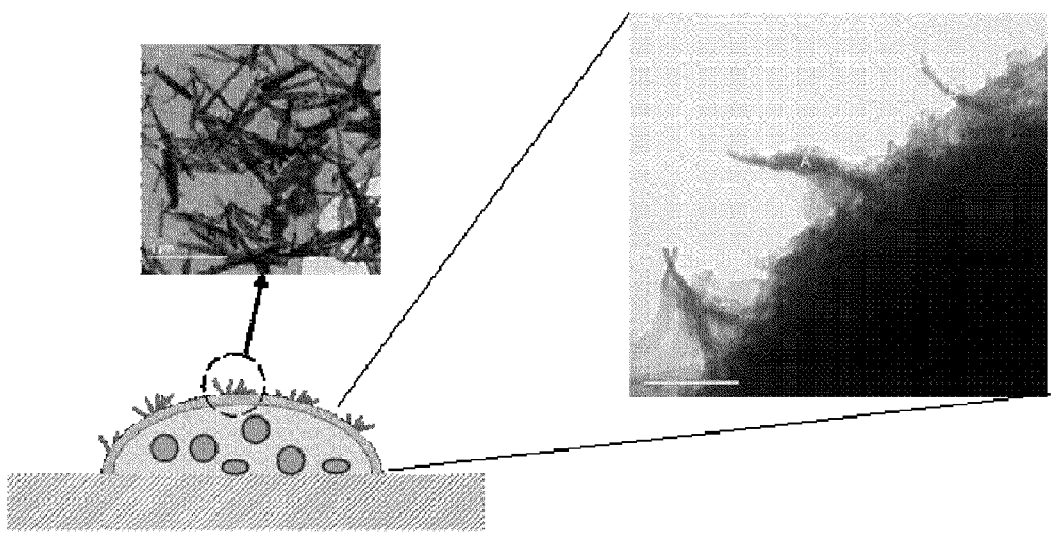
FIG. 3 is a schematic drawing of composition B coated on a surface with high magnification transmission electron micrographs of the capsule surface showing zinc-containing rod-like nanostructures (approx. 30 nm×1000 nm) protruding from the surface of the polymer encapsulant.

FIG. 3 shows a schematic drawing illustrating the detailed anatomy of the coating. The trace zinc chloride salt added in the formulation reacts with the chlorine dioxide to form in-situ the zinc-containing nano-rods embedded on the outermost surface of the capsule as shown in FIG. 3 insets. The addition of trace metal salts including zinc, copper and silver results in substantial increase in bactericidal activity (i.e., 10-100 folds).

Wiping Test

The coated surfaces were wiped thirty times with a clean cotton cloth at 20 N force normal to the surface to simulate wear. The coating was durable and remained intact even after the vigorous wiping as given in Table 1, but can be washed off with detergent water.

35° C. with the relative humidity of R.H. 60-80%. The coated samples were removed at fixed time intervals and sonicated in 20 ml deionized distilled water to dissolve the coating. An excess amount of potassium iodide (KI, BDH) was added and iodometric titration was carried out in an acidic medium. The free iodine ($I_2$) was titrated by 0.1 M sodium thiosulfate ($Na_2S_2O_3$, RDH) with starch indicator.

Figure 4:
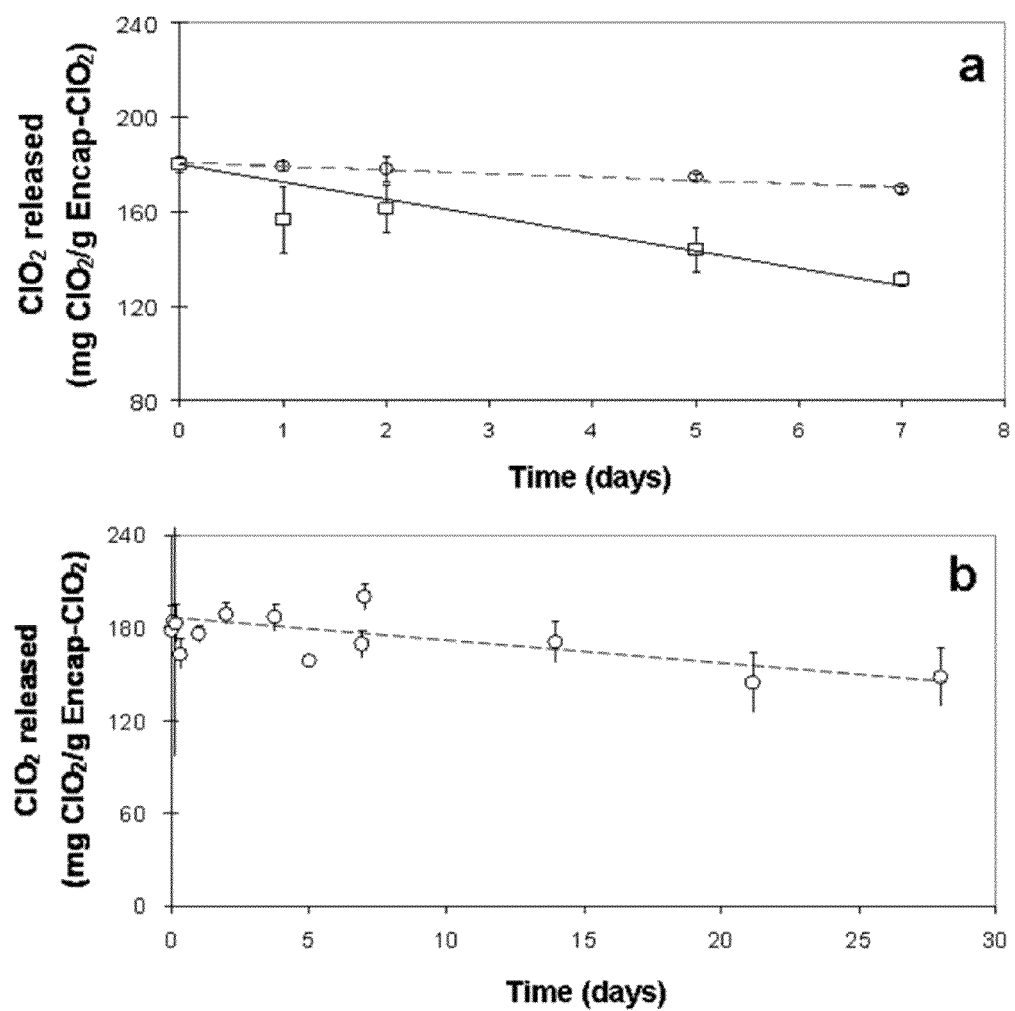
FIG. 4 is a diagram showing (a) the amount of $ClO_2$ remaining in the coating during the 7-days release experiment at 25° (○) and 35° C. (□) in a constant temperature oven with relative air humidity of 60-80% and (b) 28-days release experiment at ambient temperature (20-26° C.) and conditions (R.H.=60-90%).

FIG. 4a plots the amounts of $ClO_2$ remaining in the coating during the 7-days release experiment at 25° C. Approximately 1500 μg of gaseous $ClO_2$ was released per gram of coating material each day at 25° C. and relative humidity of R.H. 60-80%. The chlorine dioxide is released at a diffusion rate of 11 $mg·g^{-1}$ $day^{-1}$ at 35° C.

The Long Term Release of $ClO_2$

The $ClO_2$ content of the surface coating was measured at different times under ambient conditions in a ventilated laminar flow cabinet, i.e., T=20-26° C. and R.H.=60-90%. The coated samples were removed at fixed time intervals and sonicated in 20 ml deionized distilled water to dissolve the coating. An excess amount of potassium iodide (KI, BDH) was added and iodometric titration was carried out in an acidic medium. The free iodine ($I_2$) was titrated by 0.1 M sodium thiosulfate ($Na_2S_2O_3$, RDH) with starch indicator.

FIG. 4b plots the amounts of $ClO_2$ remaining in the coating during the 28-days release experiment at 25° C. Approximately 1300 μg of gaseous $ClO_2$ was released per gram of coating material each day.

The Release of $ClO_2$ Under Various Temperature

The $ClO_2$ content of the surface coating was measured at different times in an oven at a temperature of 25, 30 and 35° C. and relative humidity of R.H. 60-80%. The coated samples were removed at fixed time intervals and sonicated in 20 ml deionized distilled water to dissolve the coating. An excess amount of potassium iodide (KI, BDH) was added and iodometric titration was carried out in an acidic medium. The free iodine ($I_2$) was titrated by 0.1 M sodium thiosulfate ($Na_2S_2O_3$, RDH) with starch indicator.

Figure 5:
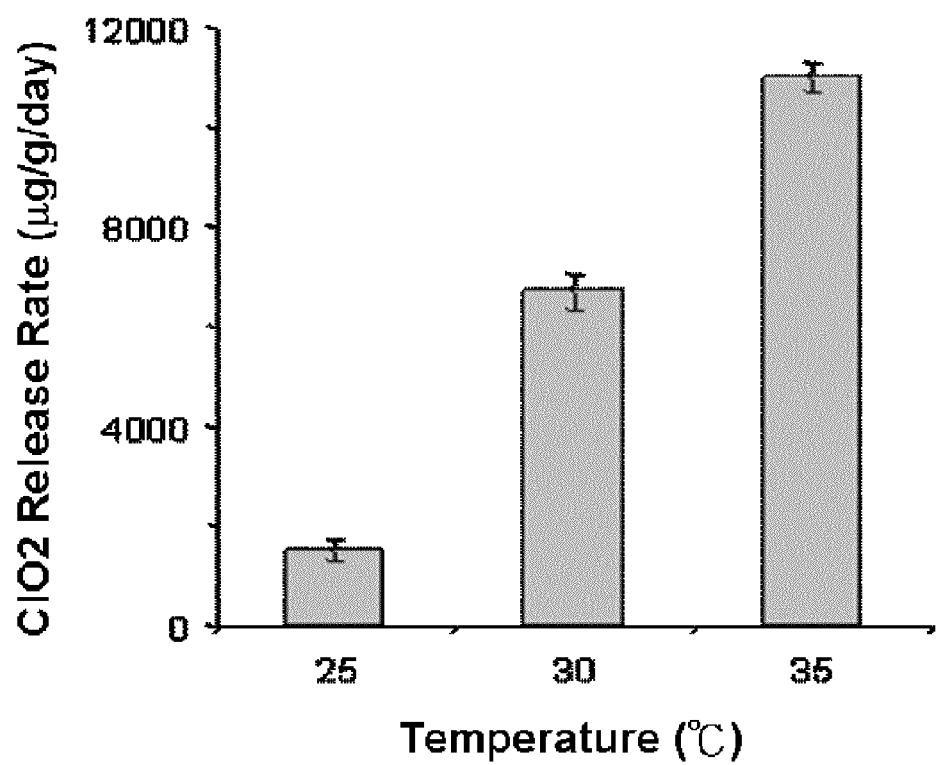
FIG. 5 is a diagram showing average release rate of $ClO_2$ gas from the coated glasses obtained over a period of 7-days.

FIG. 5 plots the average amounts of $ClO_2$ released at 25, 30 and 35° C. Elevated temperatures result in increased diffusion rate and close to the body temperature, the P123 film interface of w/o emulsion become unstable and merges with the enveloping F127 film resulting in "coalescence" and a rapid release of the biocide.

TABLE 1

| | Glass | | | | Stainless Steel | | |
| --- | --- | --- | --- | --- | --- | --- | --- |
| Elements | Uncoated | Coated | Wiped[a] | Elements | Uncoated | Coated | Wiped[a] |
| Si(2p) | 20.7 | 0.5 | 4.8 | Fe(2p) | 24.6 | 1.2 | 0.6 |
| Al(2p) | 0.6 | 0.0 | 0.0 | Cr(2p) | 6.6 | 0.7 | 0.7 |
| Mg(ls) | 5.1 | 0.0 | 0.0 | Ni(LMM) | 1.9 | 0.0 | 0.0 |
| O(ls) | 54.0 | 29.0 | 39.6 | O(ls) | 47.2 | 34.6 | 34.6 |
| Na(ls) | 6.9 | 0.5 | 5.9 | Na(ls) | 0.0 | 10.5 | 9.2 |
| C(ls) | 12.7 | 69.5 | 48.6 | C(ls) | 19.4 | 49.2 | 54.3 |

[a]Wiped 30 times in repeating motion with a cotton cloth with a 20N force normal to the surface.

Example 5

Release of $ClO_2$ from Composition A Surface Coating

The Short Term Release of $ClO_2$

The $ClO_2$ content of the surface coating was measured at different times in an oven at the temperatures of 25° C. and Example 6

Anti-Bacterial Properties of Composition A Surface Coating

Anti-bacterial Properties of Composition A against *S. aureus* Cells

The bactericidal property of the chlorine dioxide gas released from the coated glass plate was investigated for *S. aureus* cells. Sterile TSA plates were evenly inoculated with a loopful (ca. 100 μl) of *S. aureus* inoculum from the broth culture (ca. $10^6.cm^{-3}$). Glasses coated with 1 $mg·cm^{-2}$ of encapsulated $ClO_2$ were placed at fixed distances of 0.6, 3 and 10 mm from the surface of the TSA plate using sterilized U-shaped paper frames of fixed thicknesses. The TSA plate was incubated upside down for overnight at 37±0.1° C. and the agar beneath the coated glasses was examined for bacteria growth.

The polymer-encapsulated $ClO_2$ Composition A coating provided the "release-killing" property. The bactericidal activity as observed is consistent with the mass measurement data. It was observed that the 80 ppm $ClO_2$ gas concentrations near the coated surface was sufficient to prevent bacteria growth on the agar placed 0.6 mm away from the coated glass. Bacteria growth was also not observed on the agar immediately above the coated glass placed at distance of 3 mm from the surface, but at 10 mm distance, the $ClO_2$ concentration decreased sufficiently that no bactericidal activity was observed.

Anti-bacterial Properties of Composition A against Gram Positive and Gram Negative Bacteria (1)

A hundred microliters of $10^7.cm^{-3}$ bacteria cell suspension was placed in contact with the coated surface at ambient condition (23±2° C., 70% R.H.) in a sterilized biological safety cabinet (NuAire, Nu-425-400E). Three sets of runs of five samples each were carried out at the fixed contact times of 5, 10, 20, 30 and 60 min. The samples were immersed into a primary subculture tube containing 20 ml neutralizer for 30 min to stabilize the surviving bacteria cells. The sterile neutralizer solution was freshly prepared by adding 1% (v/v) 0.1 M $Na_2S_2O_3$ to 600 ml of 0.85% (w/v) normal saline (NaCl, RDH) solution containing 0.1% (v/v) (final concentration) of polyoxyethylenesorbitan monooleate (Tween 80) followed by autoclave at 121° C. for 20 min. A hundred microliters aliquots from the neutralizer were cultured on a TSA plate. The numbers of viable bacteria were counted after incubating the plates for 24 h at 37±0.1° C.

Table 2 provides the log reduction in viable bacteria after contact with 1 $mg·cm^{-2}$ coated glasses for 10 and 30 minutes on the first and seventh day for two Gram positive (i.e., *B. subtilis* and *S. aureus*) and two Gram negative (*E. coli* and *P. aeruginosa*) bacteria.

TABLE 2

Number of *B. subtilis*, *E. coli*, *P. aeruginosa* and *S. aureus* killed (in log) after contact

| Bacteria strains | Number of Bacterial Cells Killed (in log) [Percentage killed] | | |
|---|---|---|---|
| | Day 0 (t = 10 min) | Day 0 (t = 30 min) | Day 07 (t = 10 min) |
| *B. subtili* | 0.66 ± 0.07 [78.1%] | 2.70 ± 0.85 [98.8%] | 0.60 ± 0.13 [74.2%] |
| *E. coli* | 2.16 ± 0.76 [96.6%] | 5.10 ± 0.66 [99.9%] | 2.40 ± 1.76 [97.7%] |
| *P. aeruginosa* | 0.61 ± 0.17 [73.6%] | 2.00 ± 0.30 [99.2%] | 0.83 ± 0.12 [84.6%] |
| *S. aureus* | 0.46 ± 0.03 [65.1%] | 0.80 ± 0.20 [83.1%] | — |

Anti-bacterial Properties of Composition A against Gram Positive and Gram Negative Bacteria (2)

A hundred microliters of $10^7.cm^-$ bacteria cell suspension was placed in contact with the coated surface at ambient condition (23±2° C., 70% R.H.) in a sterilized biological safety cabinet (NuAire, Nu-425-400E). Three sets of runs of five samples each were carried out at the fixed contact times of 5, 10, 20, 30 and 60 min. The samples were immersed into a primary subculture tube containing 20 ml neutralizer for 30 min to stabilize the surviving bacteria cells. The sterile neutralizer solution was freshly prepared by adding 1% (v/v) 0.1 M $Na_2S_2O_3$ to 600 ml of 0.85% (w/v) normal saline (NaCl, RDH) solution containing 0.1% (v/v) (final concentration) of polyoxyethylenesorbitan monooleate (Tween 80) followed by autoclave at 121° C. for 20 min. A hundred microliters aliquots from the neutralizer were cultured on a TSA plate. The numbers of viable bacteria were counted after incubating the plates for 24 h at 37±0.1° C. The sample was drip-dried and transferred to a second subculture tube containing 20 ml of sterile nutrient broth (Nutrient broth no. 2, Oxoid) for 10 min. A hundred microliters aliquots from the nutrient broth were cultured on a TSA plate. The numbers of viable bacteria were counted after incubating the plates for 24 h at 37±0.1° C.

Figure 6A:
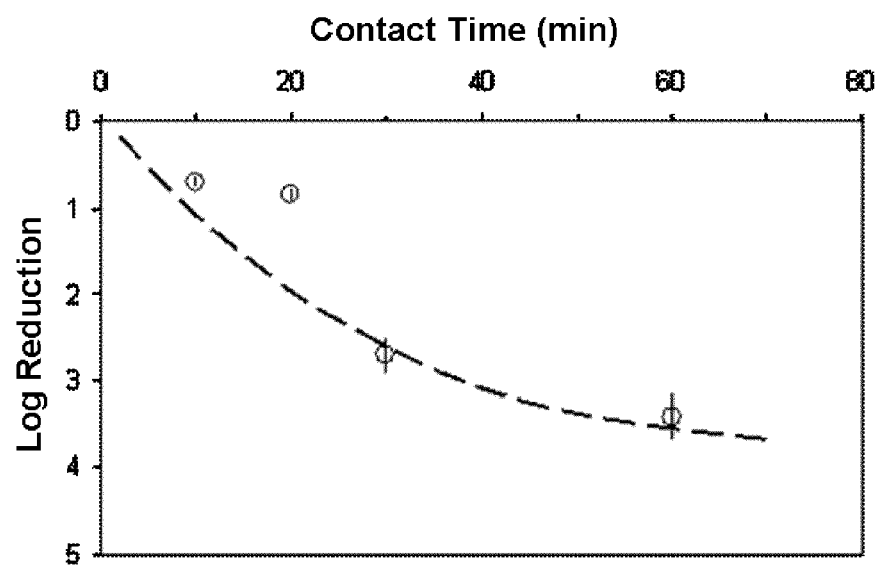
FIG. 6A is a diagram showing the log reduction in viable *B. subtilis* at various contact time.
Figure 6B:
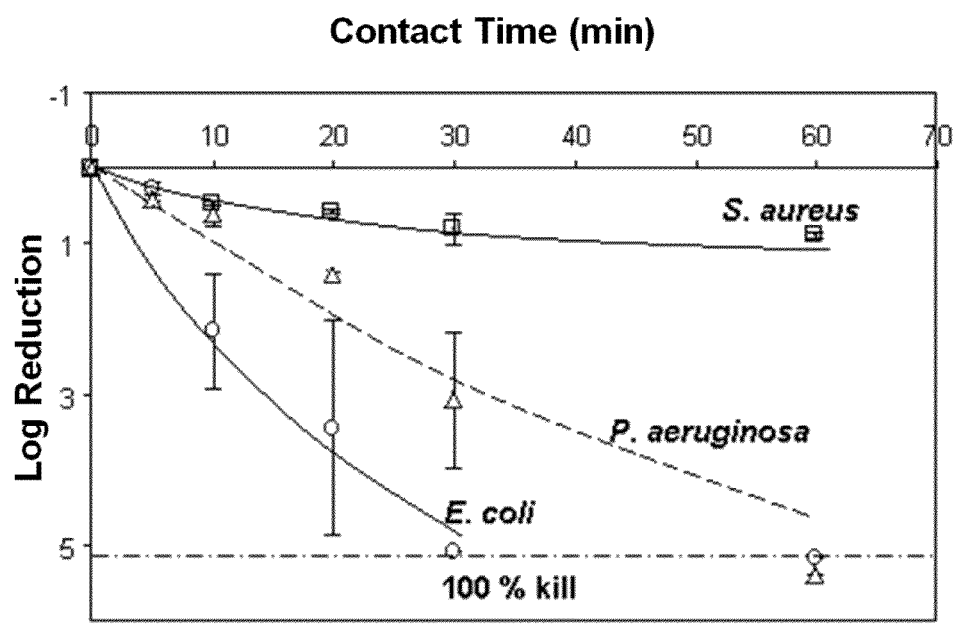
FIG. 6B is a diagram showing the log reduction in viable *E. coli, P. aeruginora* and *S. aureus* at various contact time.
Figure 6C:
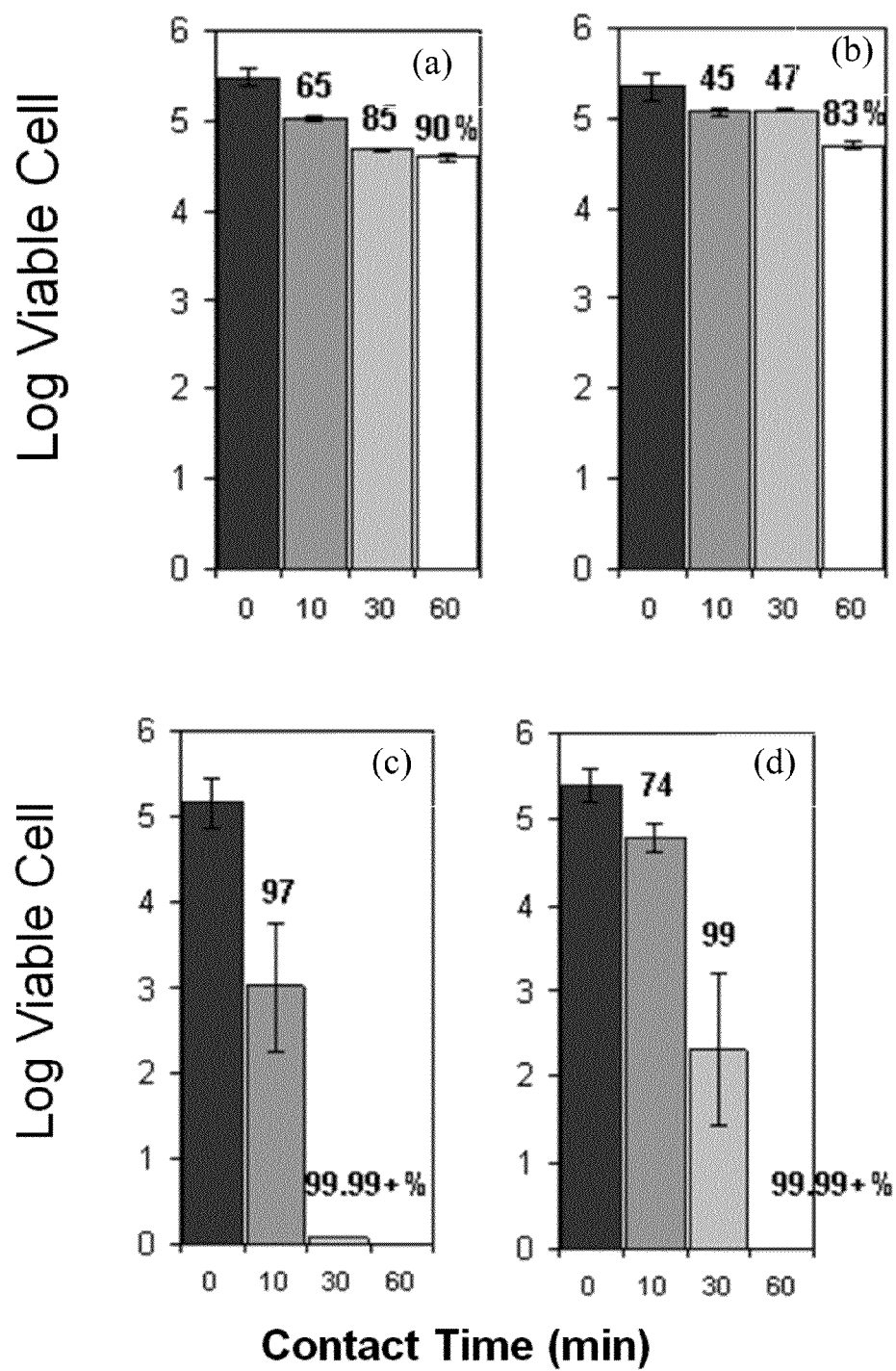
FIG. 6C shows surviving (a) *S. aureus*, (b) *S. epidermidis*, (c) *E. coli* and (d) *P. aureginosa* bacteria cells after 10, 30 and 60 minutes contact with a glass coated with 1 mg/cm² polymer-encapsulated $ClO_2$.

FIG. 6 showed plots of reduction in viable (a) *B. subtilis* and (b) *E. coli*, *P. aeruginora* and *S. aureus* as function of contact time. (c) Surviving (1) *S. aureus*, (2) *S. epidermidis*, (3) *E. coli* and (4) *P. aureginosa* bacteria cells after 10, 30 and 60 minutes contact with a glass coated with 1 $mg/cm^2$ polymer-encapsulated $ClO_2$. Percent reduction is given in the graph for each contact time. Each data was an average of three repeat experiments of five samples each.

Example 7

Antimicrobial Properties of Composition B Surface Coating

The antimicrobial w/o/w double emulsion composition B containing 30 ppm zinc chloride salt was tested for bactericidal activity against Gram positive and Gram negative bacteria.

Anti-Bacterial Properties of Composition B against Gram Positive and Gram Negative Bacteria at Various Time A hundred microliters of $10^7.cm^{-3}$ bacteria cell suspension was placed in contact with the coated surface at ambient condition (23±2° C., 70% R.H.) in a sterilized biological safety cabinet (NuAire, Nu-425-400E). Three sets of runs of five samples each were carried out at the fixed contact times of 1, 5, 10 and 30 min. The samples were immersed into a primary subculture tube containing 20 ml neutralizer for 30 min to stabilize the surviving bacteria cells. The sterile neutralizer solution was freshly prepared by adding 1% (v/v) 0.1 M $Na_2S_2O_3$ to 600 ml of 0.85% (w/v) normal saline (NaCl, RDH) solution containing 0.1% (v/v) (final concentration) of polyoxyethylenesorbitan monooleate (Tween 80) followed by autoclave at 121° C. for 20 min. A hundred microliters aliquots from the neutralizer were cultured on a TSA plate. The numbers of viable bacteria were counted after incubating the plates for 24 h at 37±0.1° C. The sample was drip-dried and transferred to a second subculture tube containing 20 ml of sterile nutrient broth (Nutrient broth no. 2, Oxoid) for 10 min. A hundred microliters aliquots from the nutrient broth were cultured on a TSA plate. The numbers of viable bacteria were counted after incubating the plates for 24 h at 37±0.1° C.

Figure 7:
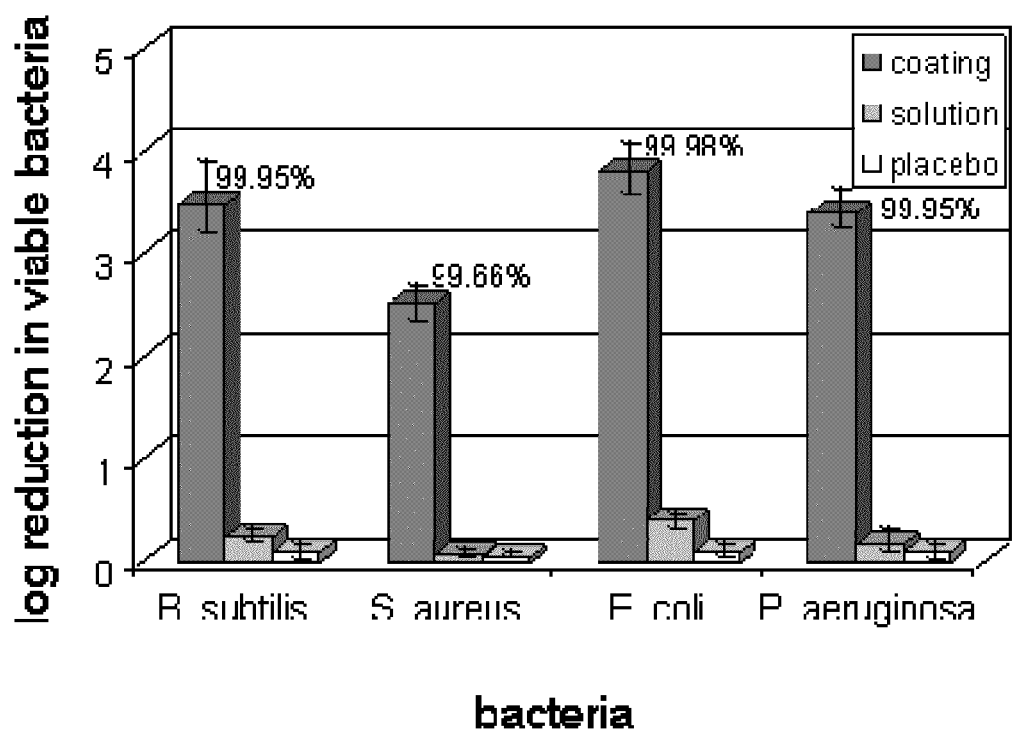
FIG. 7 is a diagram showing the log reductions in viable Gram positive and Gram negative bacteria after 10 min contact with surface coated with the antimicrobial w/o/w double emulsion composition B containing 30 ppm zinc chloride salt (coating), chlorine dioxide (solution) and encapsulated water (placebo).

FIG. 7 plots the log reduction in viable Gram positive and Gram negative bacteria after 10 min contact with surface coated with the antimicrobial w/o/w double emulsion composition B containing 30 ppm zinc chloride salt (coating), chlorine dioxide (solution) and encapsulated water (placebo). The antimicrobial composition B with 30 ppm zinc chloride attained better than 99% reduction in viable bacteria after 10 min contact with the coated surface. The figure also clearly shows that without encapsulation chlorine dioxide evaporated and becomes ineffective, nor could the polymer surfactants alone garner high antimicrobial effect.

Figure 8:
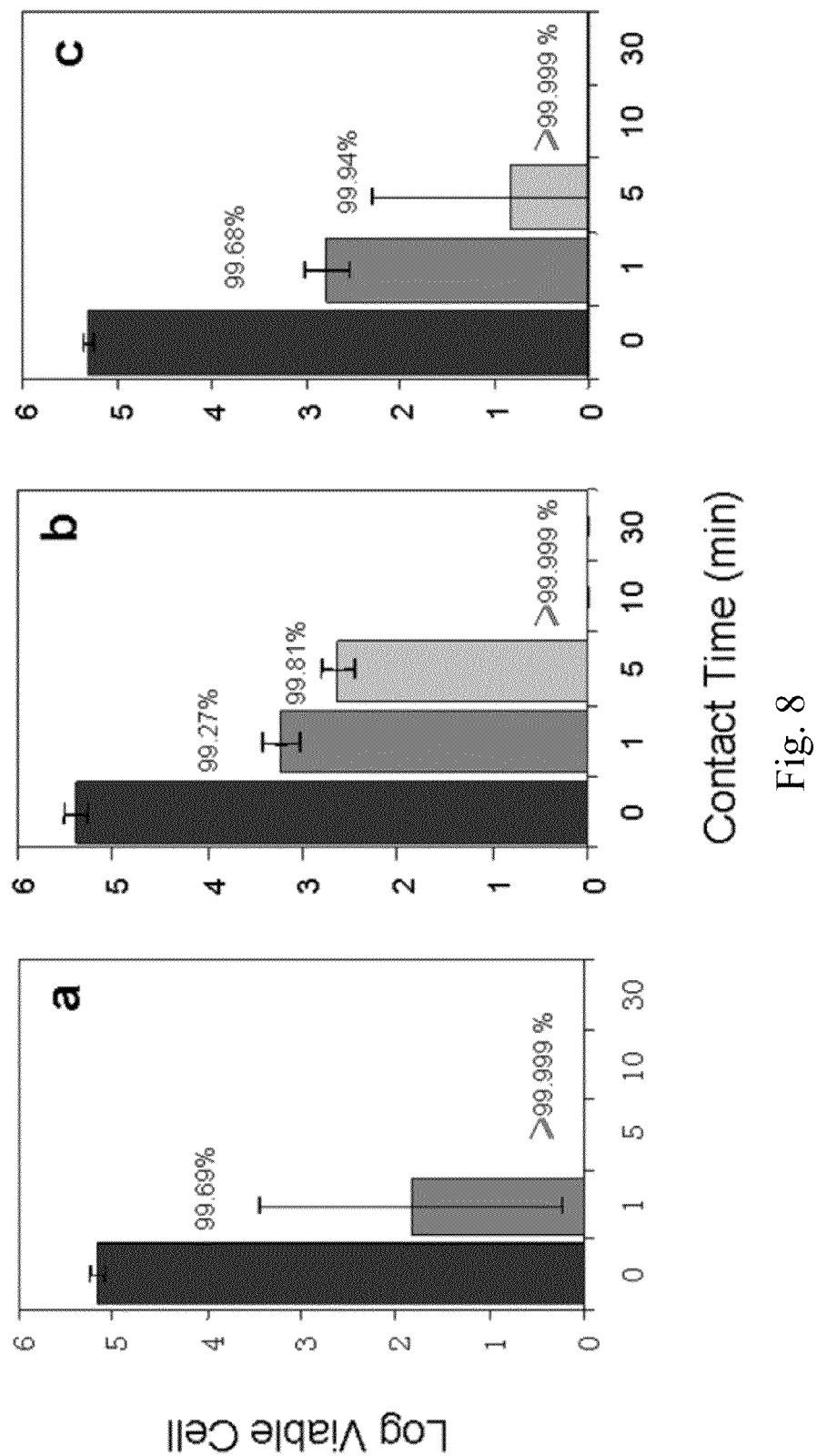
FIG. 8 is a diagram showing surviving (a) B. subtilis, (b) S. aureus and (c) E. coli bacteria cells after 1, 5, 10 and 30 minutes contact with a glass coated with 1 mg/cm$^2$ multilevel antimicrobial coating. The error bars represent the standard deviation from five samples.

FIG. 8 plots the viable bacteria cell after 1, 5, 10 and 30 min contact with glass surfaces coated with 1 mg·cm$^{-2}$ antimicrobial composition B with 30 ppm zinc chloride. The results show that the coating has an excellent bactericidal properties and 5 log reduction in viable bacteria (i.e., 99.999% kill) as obtained at a contact time of 10 min or less.

Anti-Bacterial Properties of Composition A and B against Gram Positive and Gram Negative Bacteria at Various Time Glass plates coated with antimicrobial compositions A and B were examined for bactericidal activity at various times after coating. A hundred microliters of $10^7$.cm$^{-3}$ bacteria cell suspension was placed in contact with the coated surface at ambient condition (23±2° C., 70% R.H.) in a sterilized biological safety cabinet (NuAire, Nu-425-400E). Three sets of runs of five samples each were carried out at the fixed contact times of 30 min. The samples were immersed into a primary subculture tube containing 20 ml neutralizer for 30 min to stabilize the surviving bacteria cells. The sterile neutralizer solution was freshly prepared by adding 1% (v/v) 0.1 M $Na_2S_2O_3$ to 600 ml of 0.85% (w/v) normal saline (NaCl, RDH) solution containing 0.1% (v/v) (final concentration) of polyoxyethylenesorbitan monooleate (Tween 80) followed by autoclave at 121° C. for 20 min. A hundred microliters aliquots from the neutralizer were cultured on a TSA plate. The numbers of viable bacteria were counted after incubating the plates for 24 h at 37±0.1° C. The sample was drip-dried and transferred to a second subculture tube containing 20 ml of sterile nutrient broth (Nutrient broth no. 2, Oxoid) for 10 min. A hundred microliters aliquots from the nutrient broth were cultured on a TSA plate. The numbers of viable bacteria were counted after incubating the plates for 24 h at 37±0.1° C.

Figure 9:
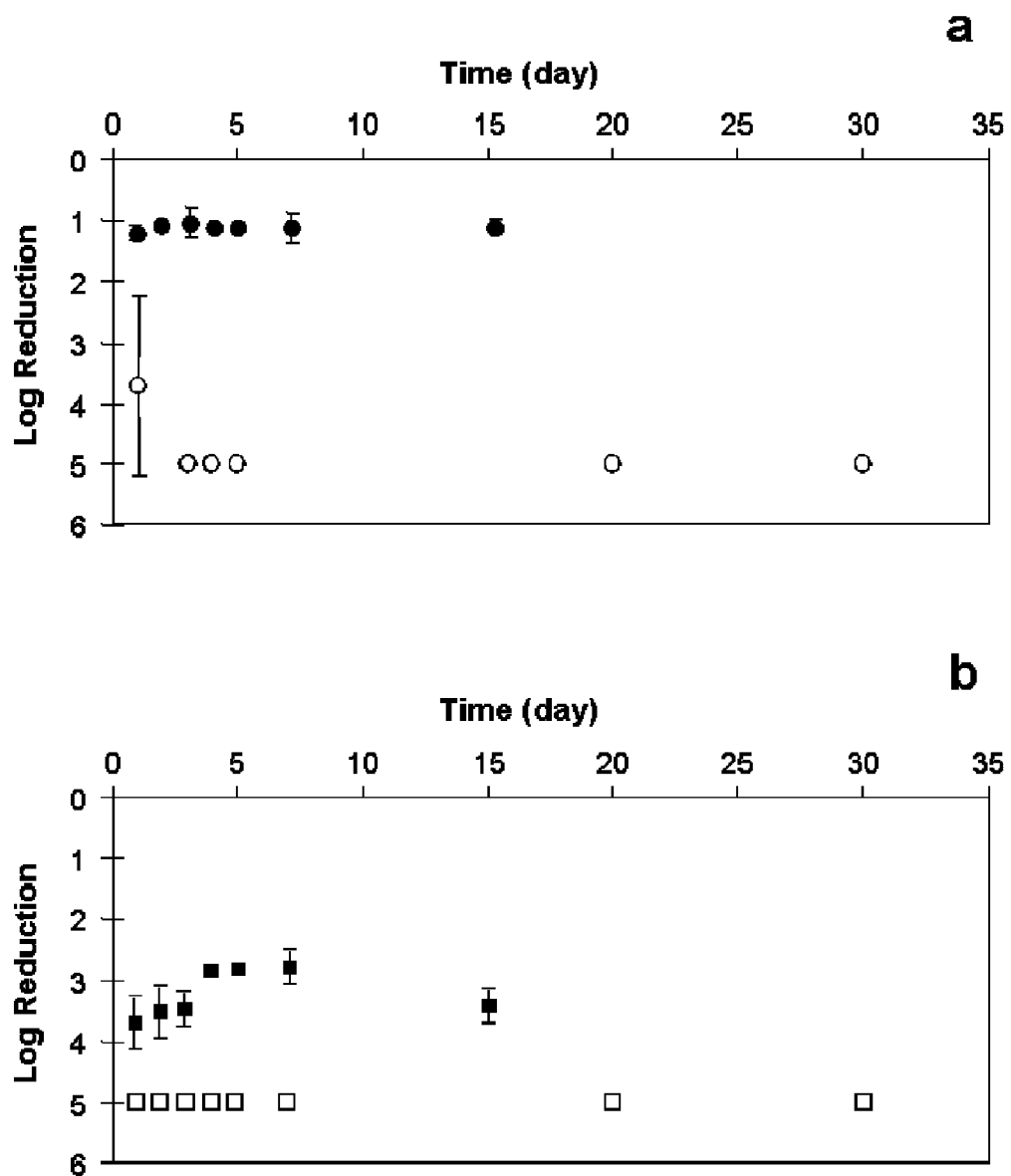
FIG. 9 is a diagram showing number of (a) S. aureus and (b) E. coli bacteria cells killed on contact with glass coated with 1 mg/cm$^2$ antimicrobial composition A (filled symbols) and B containing 30 ppm zinc chloride (open symbols) at different days after coating (30 min contact time, neutral pH). Each data were obtained from at least five samples and some of the data points were repeated more than once.

FIG. 9 compares the bactericidal property of glasses coated with multilevel antimicrobial compositions A and B for twenty-eight days. The figure plots the log reduction in viable S. aureus (FIG. 9a) and E. coli bacteria (FIG. 9b) after 30 min in contact with the coated glasses. The glasses coated with the antimicrobial composition B maintains a 5 log reduction in viable bacteria over 28 days and provides an effective and long-term surface disinfection.

Example 8

Kirby-Bauer Disk-Diffusion Test on S. aureus

Standard Kirby-Bauer disk diffusion test was performed using S. aureus. Sterile TSA plates were evenly inoculated with a loopful (ca. 100 µl) of S. aureus inoculum from the broth culture (ca. $10^6$.cm$^{-3}$). Sterile filter paper was coated with 100 µl of sterile distilled water, 70% ethanol and antimicrobial composition B. After drying, the filter was placed on the TSA plate and incubated upside down for overnight at 37±0.1° C. A filter paper coated with 100 µl of 70% ethanol without drying was used as positive control The Kirby-Bauer disk diffusion test was conducted, a standard antimicrobial test method using impregnated wafers to test whether particular bacteria are susceptible by comparing the area of clearing that surrounds the wafer where bacteria are not capable of growing (called a zone of inhibition). The zone of inhibition is largest for the wafer coated with antimicrobial composition B and dried, followed by the wafer with 70% alcohol, while both wafers with 70% alcohol (dried) and sterilized water (dried) do not show zones of inhibition.

Example 9

Release of $ClO_2$ and Antimicrobial Properties of Composition B with Zinc Chloride Surface Coating Releasing of Encapsulated $ClO_2$ from Composition B The $ClO_2$ content of the surface coating was measured at different times under ambient conditions in a ventilated laminar flow cabinet, i.e., T=20-26° C. and R.H.=60-90%. The coated samples were removed at fixed time intervals and sonicated in 20 ml deionized distilled water to dissolve the coating. An excess amount of potassium iodide (KI, BDH) was added and iodometric titration was carried out in an acidic medium. The free iodine ($I_2$) was titrated by 0.1 M sodium thiosulfate ($Na_2S_2O_3$, RDH) with starch indicator.

Figure 10:
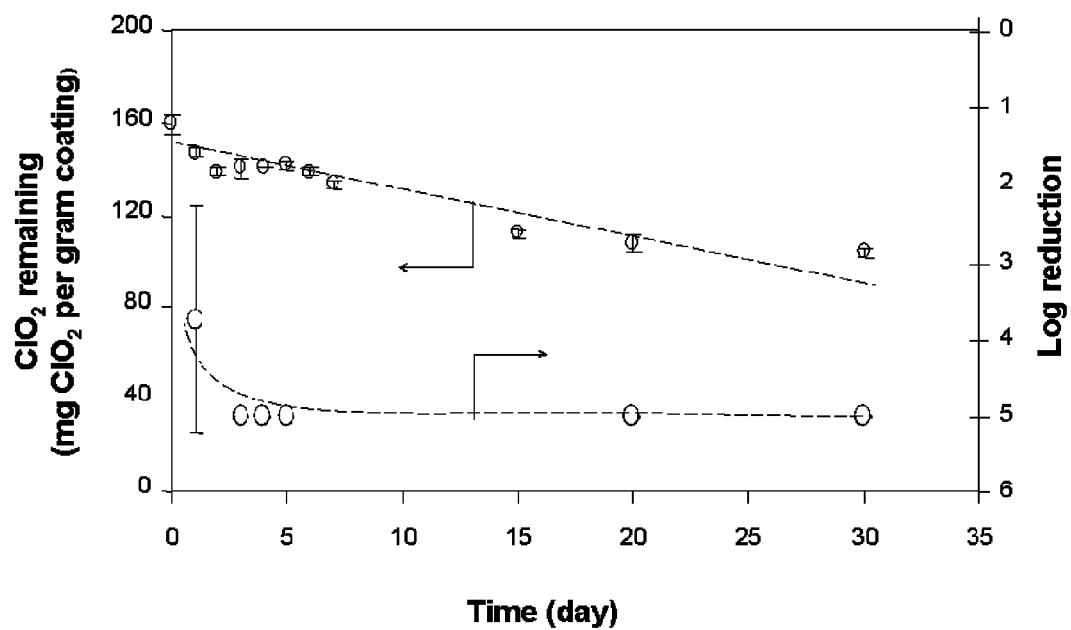
FIG. 10 is a diagram showing that the chlorine dioxide release could be obtained by monitoring the chlorine dioxide content in the antimicrobial coating with zinc as function of time and its maintain ≥99.9% reduction in viable S. aureus after 10 min contact over the entire 30 days of test at room conditions.

FIG. 10 plots the amounts of $ClO_2$ remaining in the coating during the 28-days release experiment at 25° C. Approximately 1600 µg of gaseous $ClO_2$ was released per gram of coating material each day.

Anti-Adhesive Property of Composition B

Glass plates coated with antimicrobial compositions B were examined for bactericidal activity at various times after coating. A hundred microliters of $10^7$.cm$^{-3}$ bacteria cell suspension was placed in contact with the coated surface at ambient condition (23±2° C., 70% R.H.) in a sterilized biological safety cabinet (NuAire, Nu-425-400E). Three sets of runs of five samples each were carried out at the fixed contact times of 10 min. The samples were immersed into a primary subculture tube containing 20 ml neutralizer for 30 min to stabilize the surviving bacteria cells. The sterile neutralizer solution was freshly prepared by adding 1% (v/v) 0.1 M $Na_2S_2O_3$ to 600 ml of 0.85% (w/v) normal saline (NaCl, RDH) solution containing 0.1% (v/v) (final concentration) of polyoxyethylenesorbitan monooleate (Tween 80) followed by autoclave at 121° C. for 20 min. A hundred microliters aliquots from the neutralizer were cultured on a TSA plate. The numbers of viable bacteria were counted after incubating the plates for 24 h at 37±0.1° C. The sample was drip-dried and transferred to a second subculture tube containing 20 ml of sterile nutrient broth (Nutrient broth no. 2, Oxoid) for 10 min. A hundred microliters aliquots from the nutrient broth were cultured on a TSA plate. The numbers of viable bacteria were counted after incubating the plates for 24 h at 37±0.1° C.

As shown in FIG. 10, the glasses coated with antimicrobial B with zinc chloride for twenty-eight days provided the bactericidal property. The figure plots the log reduction in viable S. aureus after 10 min in contact with the coated glasses. The glasses coated with the antimicrobial composition B maintained a 4-5 log reduction in viable bacteria over 28 days and provided an effective and long-term surface disinfection.

Example 10

Enhancement of the Bactericidal Properties of the Antimicrobial Composition B with Addition of Trace Zinc Chloride A hundred microliters of $10^7.cm^{-3}$ bacteria cell suspension was placed in contact with the coated surface at ambient condition (23±2° C., 70% R.H.) in a sterilized biological safety cabinet (NuAire, Nu-425-400E). Three sets of runs of five samples each were carried out at the fixed contact times of 1, 5, 10, 20, 30 and 60 min. The samples were immersed into a primary subculture tube containing 20 ml neutralizer for 30 min to stabilize the surviving bacteria cells. The sterile neutralizer solution was freshly prepared by adding 1% (v/v) 0.1 M $Na_2S_2O_3$ to 600 ml of 0.85% (w/v) normal saline (NaCl, RDH) solution containing 0.1% (v/v) (final concentration) of polyoxyethylenesorbitan monooleate (Tween 80) followed by autoclave at 121° C. for 20 min. A hundred microliters aliquots from the neutralizer were cultured on a TSA plate. The numbers of viable bacteria were counted after incubating the plates for 24 h at 37±0.1° C. The sample was drip-dried and transferred to a second subculture tube containing 20 ml of sterile nutrient broth (Nutrient broth no. 2, Oxoid) for 10 min. A hundred microliters aliquots from the nutrient broth were cultured on a TSA plate. The numbers of viable bacteria were counted after incubating the plates for 24 h at 37±0.1° C.

Figure 11:
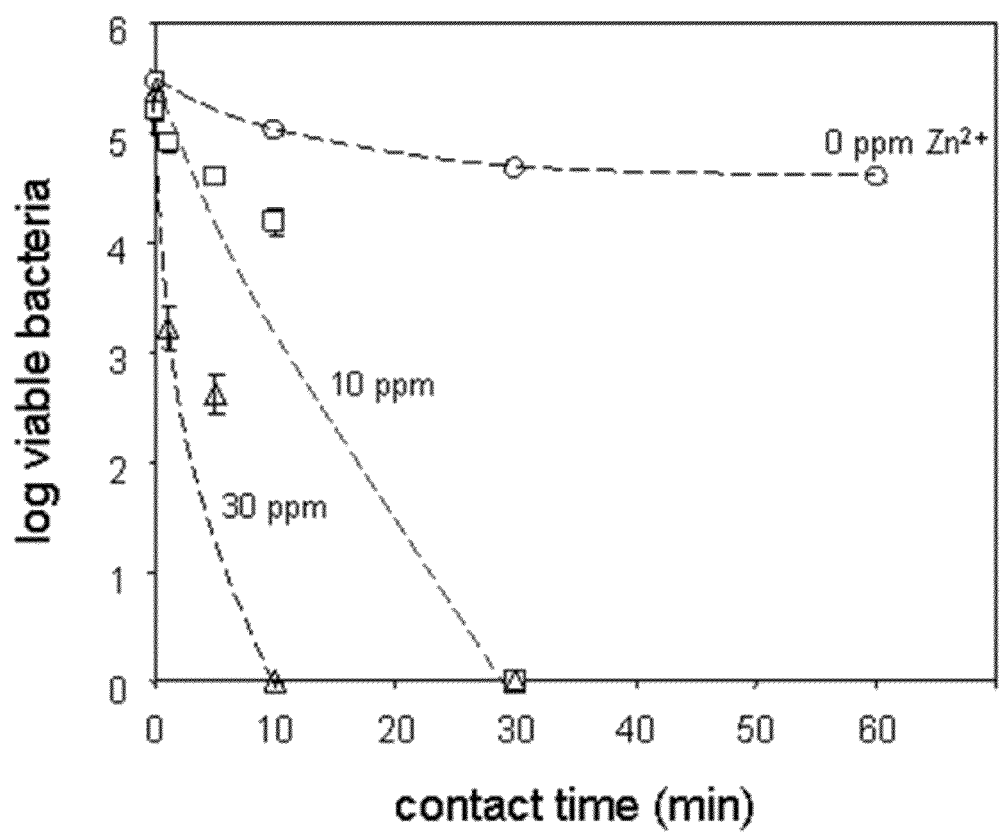
FIG. 11 is a diagram showing surviving S. aureus bacteria cells after 1, 5, 10 and 30 minutes contact with a glass coated with 1 mg/cm$^2$ antimicrobial composition B with 0, 10 and 30 ppm zinc chloride. The error bars represent the standard deviation from five samples.

As shown in FIG. 11, the addition of trace amount of zinc chloride salt in the antimicrobial composition B had a large promoting effect on the antimicrobial property of the coating. A $10^5$ reduction in viable bacterial was observed for antimicrobial composition with 30 ppm zinc chloride after 10 min contact with the coated glass surface.

Example 11

Antimicrobial Properties of Composition B containing Trace Zinc, Copper and Silver Salts Antimicrobial w/o/w double emulsion composition B containing 30 ppm cupper chloride and 30 ppm silver nitrate were prepared according to procedure described in Example 2.

A hundred microliters of $10^8.cm^3$ bacteria cell suspension was placed in contact with the coated surface at ambient condition (23±2° C., 70% R.H.) in a sterilized biological safety cabinet (NuAire, Nu-425-400E). Three sets of runs of five samples each were carried out at the fixed contact times of 10 min. The samples were immersed into a primary subculture tube containing 20 ml neutralizer for 30 min to stabilize the surviving bacteria cells. The sterile neutralizer solution was freshly prepared by adding 1% (v/v) 0.1 M $Na_2S_2O_3$ to 600 ml of 0.85% (w/v) normal saline (NaCl, RDH) solution containing 0.1% (v/v) (final concentration) of polyoxyethylenesorbitan monooleate (Tween 80) followed by autoclave at 121° C. for 20 min. A hundred microliters aliquots from the neutralizer were cultured on a TSA plate. The numbers of viable bacteria were counted after incubating the plates for 24 h at 37±0.1° C. The sample was drip-dried and transferred to a second subculture tube containing 20 ml of sterile nutrient broth (Nutrient broth no. 2, Oxoid) for 10 min. A hundred microliters aliquots from the nutrient broth were cultured on a TSA plate. The numbers of viable bacteria were counted after incubating the plates for 24 h at 37±0.1° C.

The tests indicated that antimicrobial composition B with 30 ppm copper chloride reduces $10^7$ *E. coli* by 99% and $10^7$ *B. subtilis* by >99.999% after 10 min contact with the coated glass substrate. The antimicrobial composition B with 30 ppm silver nitrate reduces $10^7$ *E. coli* by and $10^7$ *B. subtilis* by >99.999% after 10 min contact with the coated glass substrate.

Example 12

Analysis of Cell Membrane Damage

Malondialdehyde (MDA) Test

The level of malondialdehyde (MDA) produced by peroxidation of membrane lipid is considered to be indicative of the oxidative stress and membrane damage caused by $ClO_2$. The MDA was measured by thiobarbituric acid assay (Esterbauer, H. & Cheeseman, K. H.; *Methods Enzymol.* 1990, 186, 407-421).

A hundred microliters of $10^7.cm^{-3}$ *B. subtilis* cell suspension was deposited on the glass substrate coated with antimicrobial composition A and allowed 10 min contact. The bacteria was recovered and mixed with 5% trichloroacetic acid (99.0%, Sigma-Aldrich) in an eppendorf tube, before adding 0.6% 2-thiobarbituric acid (98%, Sigma). The solution was heated to 95° C. for 15 min, cooled to room temperature and centrifuged (Eppendorf 5415C) at 10,000 rpm for 10 min. The optical density of the supernatant was recorded between 534 nm and 600 nm by a spectrophotometer (ICN Biomedicals, 156812) and the MDA concentration was calculated against calibration standards.

Figure 12:
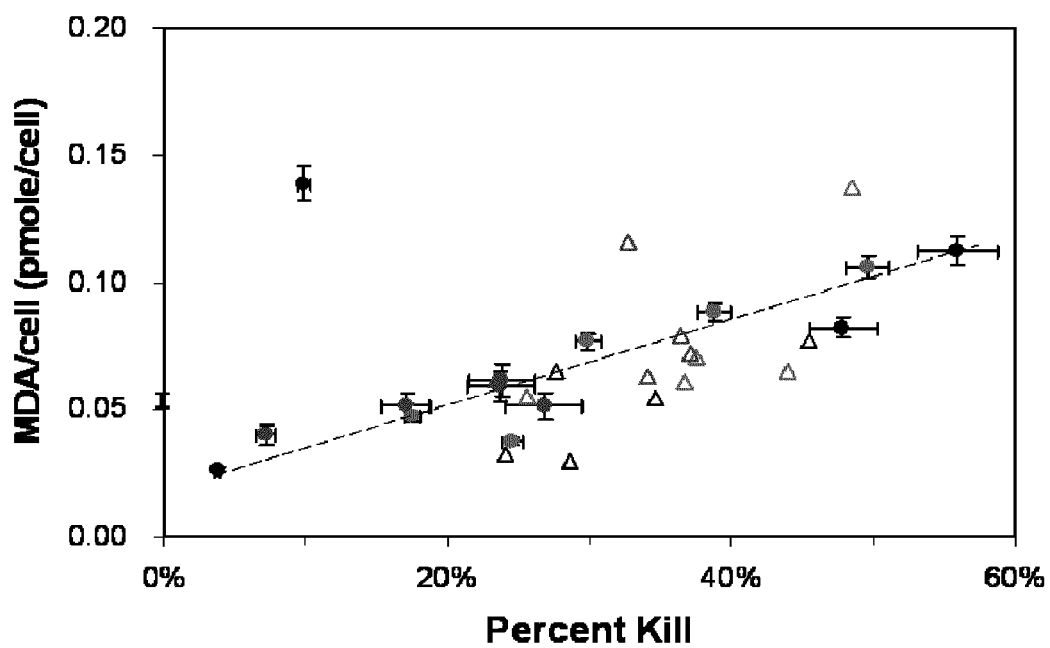
FIG. 12 is a diagram showing malondialdehyde (MDA) level in viable B. subtilis cells after contact with glasses coated with antimicrobial composition A (filled symbols) and sprayed on ClO$_2$ (open symbols) for different lengths of time.

As shown in FIG. 12, there was a strong correlation between increased MDA level and cell death indicating that the membrane damage was one of possible routes that the coating inactivated and killed microorganisms.

Observation of Membrane Damages on Bacteria Cells by Atomic Force Microscopy

A 100 μl antimicrobial w/o/w double emulsion composition B containing 30 ppm zinc chloride was deposited on a 1 inch² clean and sterile silicon wafer. A 100 μl of $10^7.cm^{-3}$ *E. coli* was deposited on the coated wafer and observed under an atomic force microscope (Nanoscope IIIα) under tapping mode.

It was observed that as compared with a healthy *E. coli* cell on clean and sterile silicon surface, the cell and membrane of an *E. coli* cell in contact with antimicrobial composition B coated silicon were damaged. This further indicates that the antimicrobial composition damages the bacteria cell.

Example 13

Anti-Adhesive Property of the Antimicrobial w/o/w Double Emulsion

The adhesion of *E. coli* K12 (Carolina 15-5065A) and *S. aureus* on clean glass and glass coated with antimicrobial w/o/w double emulsion composition A with 0 ppm chlorine dioxide (i.e., placebo) was determined. Two hundred microliters of $10^8$ cm⁻³ bacteria suspensions were uniformly spread on the coated and uncoated glass surface and incubated at 37° C. for 4 h without shaking. The samples were washed gently with sterile distilled water to remove non-adherent bacteria. Gram staining was performed on the samples and images observed under the optical microscope (magnification of 1000×) were recorded to quantify the degree of bacteria adhesion on the coated and uncoated surfaces.

Figure 13:
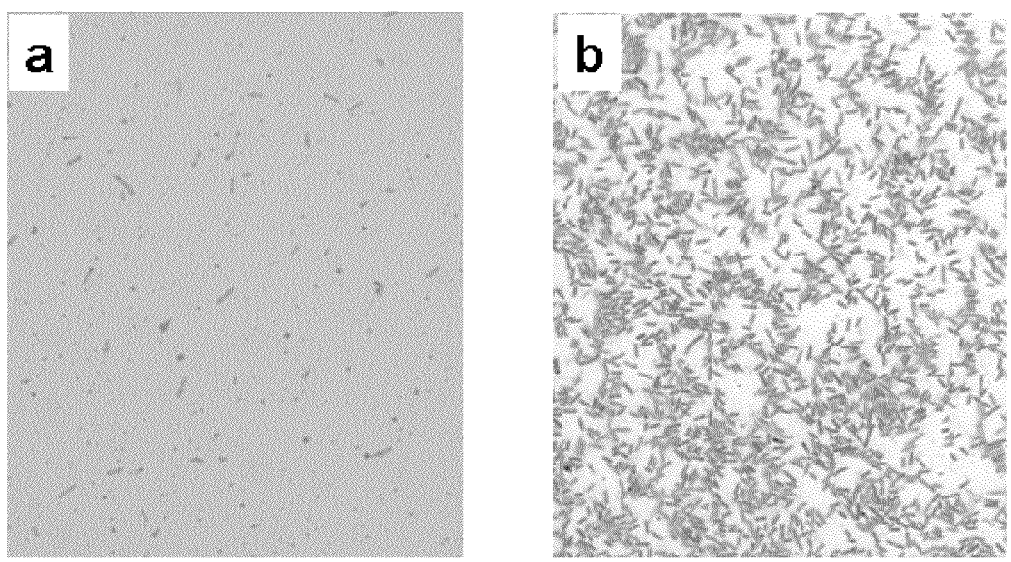
FIG. 13 is an optical image of adherrent E. coli cells on (a) glass coated with encapsulated sterile water (i.e., placebo) and (b) uncoated glass at a magnification of 1000×.

As shown in FIG. 13, the number of *E. coli* on the coated glass was significantly less compared to uncoated glass. This indicated that the coating prevented the adhesion of the bacteria.

Figure 14:
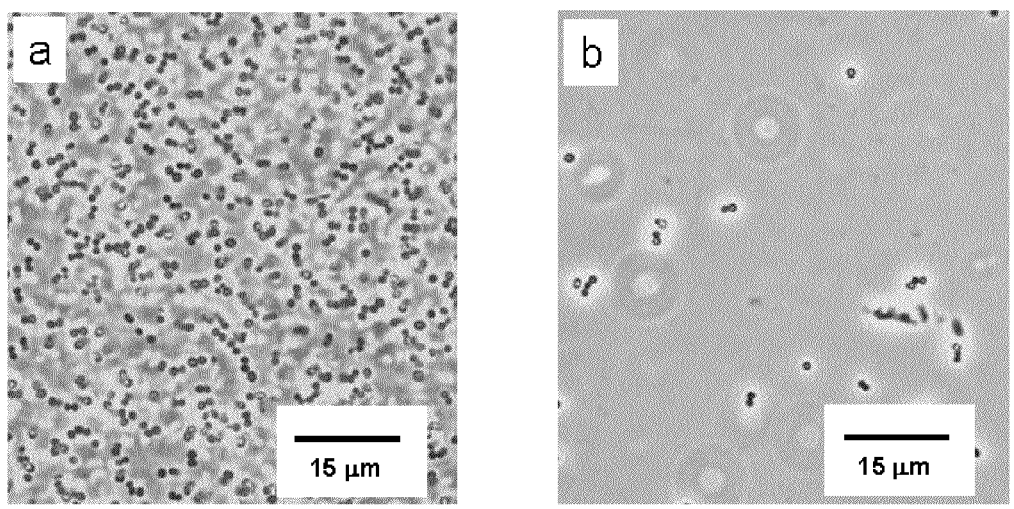
FIG. 14 is an optical image of adherrent S. aureus cells on (a) glass coated with encapsulated sterile water (i.e., placebo) and (b) uncoated glass at a magnification of 1000×.

As shown in FIG. 14, the number of *S. aureus* on the coated glass was significantly less compared to uncoated glass. The placebo coating demonstrated that the polymers used in the encapsulation promoted anti-adhesion properties.

Example 14

Sporicidal Property of the Antimicrobial w/o/w Double Emulsion Composition A and C Preparation of *B. subtilis* Endospores The *B. subtilis* (Carolina 15-4921A) bacteria cells were cultivated on TSA plates at 37±0.1° C. for 3 days to obtain higher spore yield. One or two bacterial colonies were harvested from the plates and transferred to a 15 ml centrifuge tube containing 5 ml sterilized deionized water. The suspension was mixed with a vortex to segregate the cells and spores. Two milliliters of the suspension was then transferred to an Eppendorf tube. The spores were purified by centrifugation and water washing. The suspension was centrifuged at 10,000 g for 20 min at 4° C. The supernatant was decanted and 1 ml of cold sterilized deionized water (4° C.) was added and the sample re-suspended at 4° C. An aliquot of the suspension was examined under a phase contrast microscope. The centrifugation and washing steps were repeated until more than 99% free spores were obtained as indicated by the phase contrast microscopy. The purified spores were suspended in a phosphate buffered saline (pH 7.4) and stored in the dark at 4° C. for no more than 7 days. The concentration of the viable spores in the suspension was determined by plate counting technique on TSA plates following a serial dilution of an aliquot of the suspension.

Sporicidal Test

A hundred microliters of $10^5.cm^{-3}$ *B. subtilis* (Carolina 15-4921A) endospores suspension was placed in contact with coated and uncoated glass substrates at ambient condition (23±2° C., 70% R.H.) in a sterilized biological safety cabinet (NuAire, Nu-425-400E). Measurements were made from a set of five samples for each contact times of 0.5, 2, 8, 24, 48 and 72 h. After the required contact time, the substrates were immersed in 20 ml neutralizer for 30 min to stabilize the surviving bacteria followed by 20 ml of nutrient broth for 10 min. The numbers of viable spores were determined by plate spreading method onto TSA plates. The plates were incubated overnight at 37° C. and the number of colonies counted.

Figure 15:
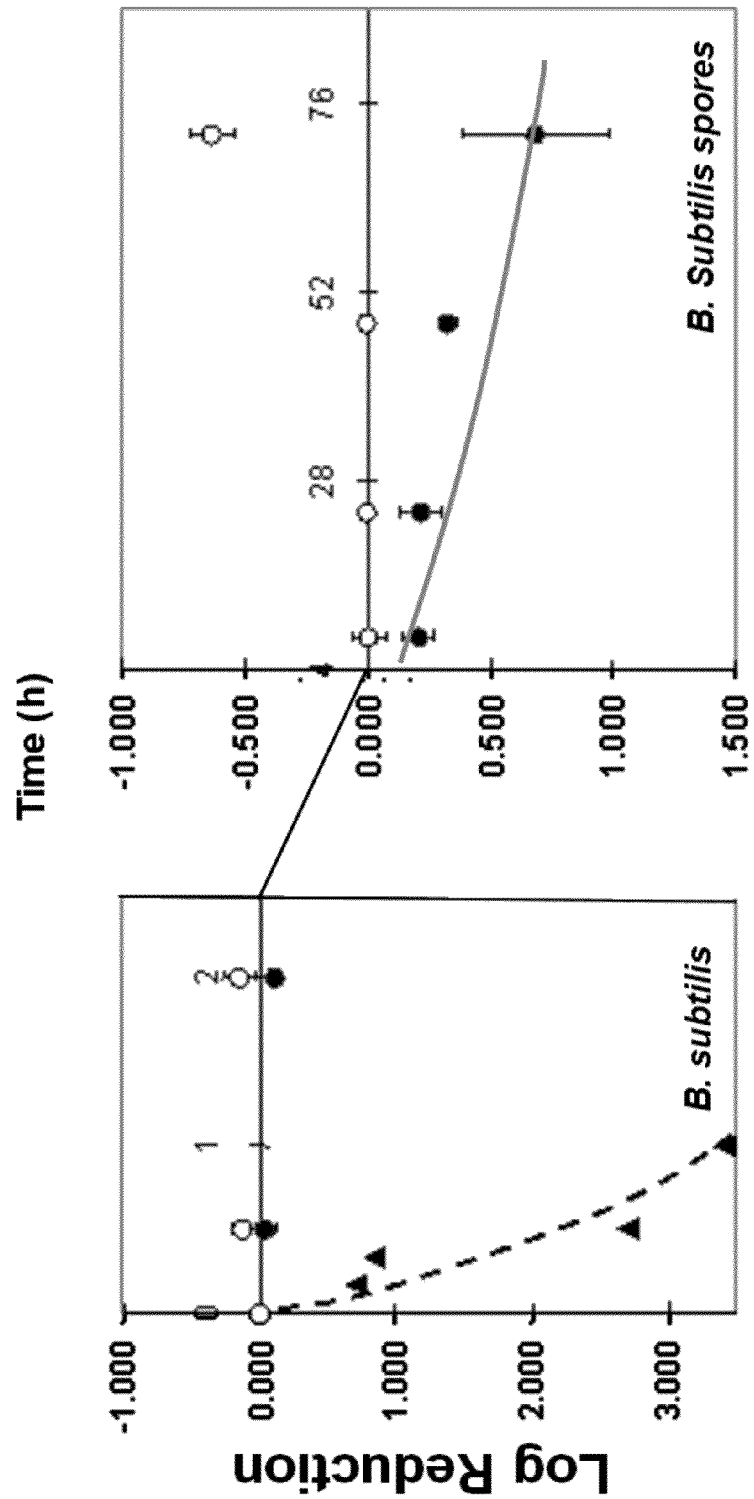
FIG. 15 is a diagram showing the reduction profile of the tested endospores and cells of B. subtilis with respect to the contact time on glasses coated with 1 mg cm$^{-2}$ antimicrobial w/o/w double emulsion composition A (solid symbols) compared with those on glass without the coating (open symbol). Each data point represents the mean of triplicate sets of five samples with the standard error bar.

FIG. 15 plots the log reduction of viable *B. subtilis* vegetative cells and endospores in contact with glasses coated with antimicrobial w/o/w double emulsion composition A.

The sporicidal properties of glasses coated with antimicrobial w/o/w double emulsion composition C displays better than 90% reduction after 30 min contact. The enhanced performance was attributed to formation of metal-containing nanostructures and the oxidative copper-ascorbic acid dyad reaction that damaged the endospores.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for preparing a material in the form of liquid for forming an antimicrobial surface coating with multi-level antimicrobial properties, comprising: encapsulating one or more volatile or gaseous biocides in two or more amphiphilic block copolymers with different hydrophilic lipophilic balances (HLBs) to obtain a water-in-oil-in-water (w/o/w) double emulsion, and mixing the w/o/w double emulsion with one or more nonvolatile biocides, each of which is selected from the group consisting of a metal containing biocide, triclosan, a carboxylic acid, a sugar acid and a combination thereof.

2. The method of claim 1, wherein each of the volatile or gaseous biocides is selected from the group consisting of dissolved chlorine dioxide, dissolved chlorine, chlorinated compounds, alcoholic and phenolic compounds, and their solid and/or liquid precursors, and a combination thereof.

3. The method of claim 1, wherein the volatile biocides are dissolved chlorine dioxide and its precursors.

4. The method of claim 1, wherein the volatile biocides are combination of dissolved chlorine dioxide, a dissolved chlorite salt and dissolved chlorine.

5. The method of claim 1, wherein the carboxylic acid is citric acid.

6. The method of claim 1, wherein the sugar acid is ascorbic acid.

7. The method of claim 1, wherein the one or more nonvolatile biocides are metal containing biocides.

8. The method of claim 7, wherein each of the metal containing biocides is selected from the group consisting of one or more of Group VII, IB, IIB, IVA and IVB metal containing compounds and salts thereof, and a combination thereof.

9. The method of claim 1, wherein the two or more amphiphilic block copolymers form an emulsion encapsulating the one or more volatile or gaseous biocides whereby said biocides may be released slowly, gradually and continuously into the surrounding environment.

10. The method of claim 1, wherein each of the amphiphilic block copolymers is an amphiphilic di- or tri-blocks copolymer.

11. The method of claim 10, wherein each of the amphiphilic block copolymers is a poloxamer or a combination thereof.

12. The method of claim 1, wherein the one or more nonvolatile biocides are encapsulated together with the one or more volatile or gaseous biocides in the polymers.

* * * * *